United States Patent [19]

Smith et al.

[11] 4,111,559
[45] Sep. 5, 1978

[54] APPARATUS FOR DETERMINING THE TRANSMISSIVITY OF AN OPTICAL MEDIUM

[75] Inventors: Chester L. Smith, Lake Hopatcong; David N. Everswick, Succasunna, both of N.J.

[73] Assignee: The United States of America as represented by the Secretary of the Army, Washington, D.C.

[21] Appl. No.: 769,601

[22] Filed: Feb. 17, 1977

[51] Int. Cl.² .................. G01N 21/22; G01N 21/26
[52] U.S. Cl. .................................. 356/201; 250/575
[58] Field of Search .................. 356/201, 212, 213; 250/573, 574, 575, 518

[56] References Cited
U.S. PATENT DOCUMENTS 3,619,624  11/1971  Sorenson .................. 356/201

OTHER PUBLICATIONS

G. T. Schappert, Technique for Measuring Visibility, 10/71, pp. 2325-2328.

Primary Examiner—Vincent P. McGraw
Assistant Examiner—Rodney B. Bovernick
Attorney, Agent, or Firm—Nathan Edelberg; Harold H. Card, Jr.; A. Victor Erkkila

[57] ABSTRACT

Three photometers are positioned at three points $P_1$, $P_2$ and $P_3$, aligned with each other and with an illuminating flare, and located at equal distances $d$ from each other, with the middle photometer at a distance D, greater than $d$, from the flare; the illuminations $E_1$, $E_2$, and $E_3$ simultaneously received by the three photometers from the flare are recorded; and the transmissivity T, or transmission per mile, of the atmosphere traversed by the light is calculated from the formula:

$$T = \left[ \sqrt{\frac{E_3}{E_2}} + \sqrt{\frac{E_3}{E_2} - \sqrt{\frac{E_3}{E_1}}} \right]^{2/d}$$

where the E values are in foot candles and $d$ is in miles.

2 Claims, 3 Drawing Figures

APPARATUS FOR DETERMINING THE TRANSMISSIVITY OF AN OPTICAL MEDIUM

GOVERNMENTAL INTEREST

The invention described herein may be manufactured, used, and licensed by or for the Government for Governmental purposes without the payment to us of any royalties thereon.

BACKGROUND AND BRIEF SUMMARY OF THE INVENTION

The present invention relates to a new and improved method of experimentally determining the transmissivity of a particular optical medium, such as a particular region of the atmosphere.

One of the major problems in the field testing of flare systems has been the effects of atmospheric attenuation of light. Methods that have been developed and utilized to measure the transmissivity of a medium are complex, costly, and difficult to set up and operate. This is particularly true in the case of a field test environment because light attenuation by the atmosphere causes extremely large errors in the determination of the source intensity.

In the past, the Army, Navy, and Air Force have relied on weather reports giving only a crude estimate of the limits of visibility to determine test conditions. Commercial transmissometers have been experimented with for assessing losses in source measurements in the field testing of flare systems and have been found to be impractical. In such cases, the complexity and cost of conducting the test or the accuracy and reliability of the data became a problem. Typically, tests simulating battlefield illumination conditions have operated neglecting atomspheric attenuation. This leads to errors in determining the intensity of the source as high as 50%.

This invention provides a method of measuring the atmospheric transmission of the actual test range (optical path) during the conduct of the test. Using this information, flare intensity measurements can then be corrected to true candlepower values. In addition, this technique utilizes equipment similar to that which has been provided for the conventional illumination measurements. Because of this, the cost and time involved with the transmission measurements are kept to a minimum. Illumination measurements in field flare testing are taken with photometers. They typically consist of a photocell-filter combination corrected to the visibility function (average response of the human eye) and associated electronics.

In accordance with the present invention: three radiation sensors, are positioned at three points $P_1$, $P_2$ and $P_3$ aligned with each other and with a radiation source, such as an illuminating flare, and located at equal known distances d from each other, with the middle sensor at a distance D, greater than d, from the source; the amounts or levels of radiation $E_1$, $E_2$, and $E_3$ simultaneously received by the three sensors from the source are recorded; and the transmissivity T, or transmission per mile, of the optical medium traversed by the radiation is calculated from the formula:

$$T = \left[ \sqrt{\frac{E_3}{E_2}} + \sqrt{\frac{E_3}{E_2} - \sqrt{\frac{E_3}{E_1}}} \right]^{2/d},$$

where the E values are in foot candles and d is in miles. Thus, the transmissivity can be determined without knowledge of either the source intensity or the distance D.

DETAILED DESCRIPTION OF A PREFERRED EMBODIMENT

Figure 1:
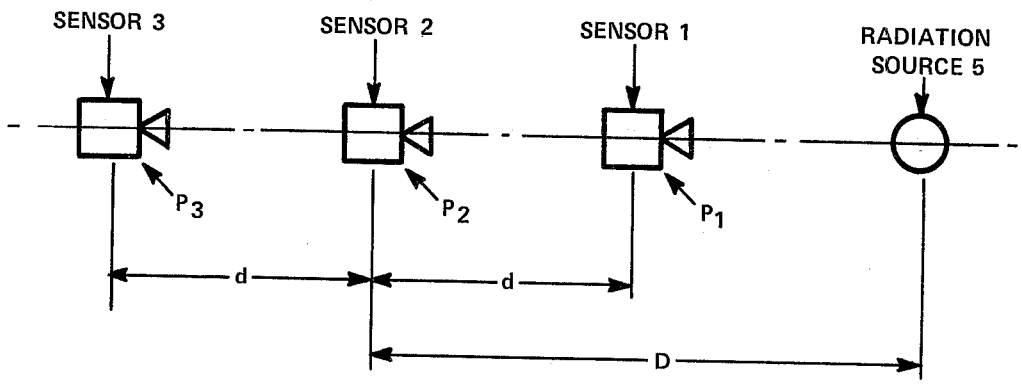
FIG. 1 is a schematic diagram of an arrangement of sensors for measuring the radiation received through the atmosphere from a radiation source at three points aligned with the source in accordance with the present invention.

As shown schematically in FIG. 1, three radiation sensors 1, 2 and 3 are mounted in line with each other and with a radiation source 5, with equal spacing d between sensors 1 and 2 and sensors 2 and 3, and with the middle sensor at a distance D, greater than d, from the source 5. For example, the sensors may be photometers of the photo-voltaic silicon barrier layer type, corrected by filters to have a spectral response equal to the average human eye, and the radiation source 5 may be an illuminating flare.

The general expression for determining the illumination level or amount of radiation at a fixed distance from a light source is $$E = I/r^2, \qquad (1)$$

where E is the illumination level in foot candles, I is the source intensity in candlepower, and r is the distance from the source in feet.

The intensity I of the source can be determined, in accordance with the invention disclosed and claimed in our copending application Ser. No. 769,602 filed Feb. 17, 1977, as follows. Using only sensors 1 and 2 of FIG. 1, the illumination $E_1$ of sensor 1 and $E_2$ of sensor 2, from equation (1), are:

$$E_1 = I/(D-d)^2 \text{ and} \qquad (1a)$$
$$E_2 = I/D^2 \qquad (1b)$$

Eliminating D from equations (1a) and (1b) and solving for I yields $$I = \left[ \frac{d}{\frac{1}{\sqrt{E_2}} - \frac{1}{\sqrt{E_1}}} \right]^2 \qquad (2)$$

Equations (1) and (2) are, of course, true only for a perfect optical medium having 100% transmissivity.

Equation (2) is modified to include atmospheric attenuation by scaling the illuminations $E_2$ and $E_1$ as a function of the transmissivity T and the distance $r$ from the source. Since T is the transmision for a unit distance in the medium, the transmission for a distance $r$ in the medium is $T^r$. It is convenient to express T as the transmission per mile, hence, the distances $r$ must be in miles. Thus, equation (2) becomes $$I^{1/2} = \left[ \frac{d \times 5280}{\frac{1}{\sqrt{\frac{E_2}{T^D}}} - \frac{1}{\sqrt{\frac{E_1}{T^{D-d}}}}} \right] \quad (3)$$

A similar equation is obtained using the illumination levels $E_2$ and $E_3$ from sensors 2 and 3, $$I^{1/2} = \left[ \frac{d \times 5280}{\frac{1}{\sqrt{\frac{E_3}{T^{D+d}}}} - \frac{1}{\sqrt{\frac{E_2}{T^D}}}} \right] \quad (4)$$

Combining equations (3) and (4) to eliminate I, yields, $$\frac{1}{\sqrt{\frac{E_3}{T^{D+d}}}} - \frac{1}{\sqrt{\frac{E_2}{T^D}}} = \frac{1}{\sqrt{\frac{E_2}{T^D}}} - \frac{1}{\sqrt{\frac{E_1}{T^{D-d}}}} \quad (5)$$

Multiplying each term of equation by $E_3/T^D$ and simplifying yields $$2\sqrt{\frac{E_3}{E_2}} = T^{d/2} + \sqrt{\frac{E_3}{E_1}}\, T^{-d/2} \quad (6)$$

Multiplying by $T^{d/2}$ and rearranging yields $$T^d - 2\sqrt{\frac{E_3}{E_2}}\, T^{\frac{d}{2}} + \sqrt{\frac{E_3}{E_1}} = 0 \quad (7)$$

Let $x^2 = T^d$ in equation (7), yielding $$x^2 - 2\sqrt{\frac{E_3}{E_2}}\, x + \sqrt{\frac{E_3}{E_1}} = 0. \quad (8)$$

Using the quadratic formula, $$x = \sqrt{\frac{E_3}{E_2}} \pm \sqrt{\frac{E_3}{E_2} - \sqrt{\frac{E_3}{E_1}}}$$

$$T = x^{2/d} = \left[ \sqrt{\frac{E_3}{E_2}} \sqrt{\frac{E_3}{E_2} - \sqrt{\frac{E_3}{E_1}}} \right]^{2/d} \quad (9)$$

Thus, the transmissivity T is a function only of the measured illumination levels $E_1$, $E_2$ and $E_3$ and the spacing $d$ in miles therebetween, being independent of the intensity I of the light source and the distance D to the light source. However, it is obvious that D be greater than $d$. For example, $d$ may be 5000 ft. with D 10,000 ft., and the intensity of the flare used as the light source may be $10^6$ candlepower. In this example, if the transmissivity of the atmosphere was 80%, or 0.8, the three sensors $S_1$, $S_2$ and $S_3$, should detect the following illumination levels using equation (1) modified to include T:

$$E_1 = \frac{IT^r}{r^2}$$

$$= \frac{10^6(.8)^{\frac{5000}{5280}}}{(5000)^2}$$

$$= .032381 \text{ foot candle,}$$

$$E_2 = \frac{10^6(.8)^{\frac{10,000}{5280}}}{(10^4)^2}$$

$$= .0065533 \text{ foot candle, and}$$

$$E_3 = \frac{10^6(.8)^{\frac{15,000}{5280}}}{(15000)^2}$$

$$= .0023578 \text{ foot candle.}$$

As a check, these values, with $d = 5000$ feet, in equation (9) yields $$T = \left[ \sqrt{\frac{.0023578}{.0065533}} + \sqrt{\frac{.0023578}{.0065533} - \sqrt{\frac{.0023578}{.0323809}}} \right]^{\frac{10560}{5000}}$$

$$= (.899734)^{2.112}$$

$$= .8 \text{ (the transmissivity assumed).}$$

Figure 2:
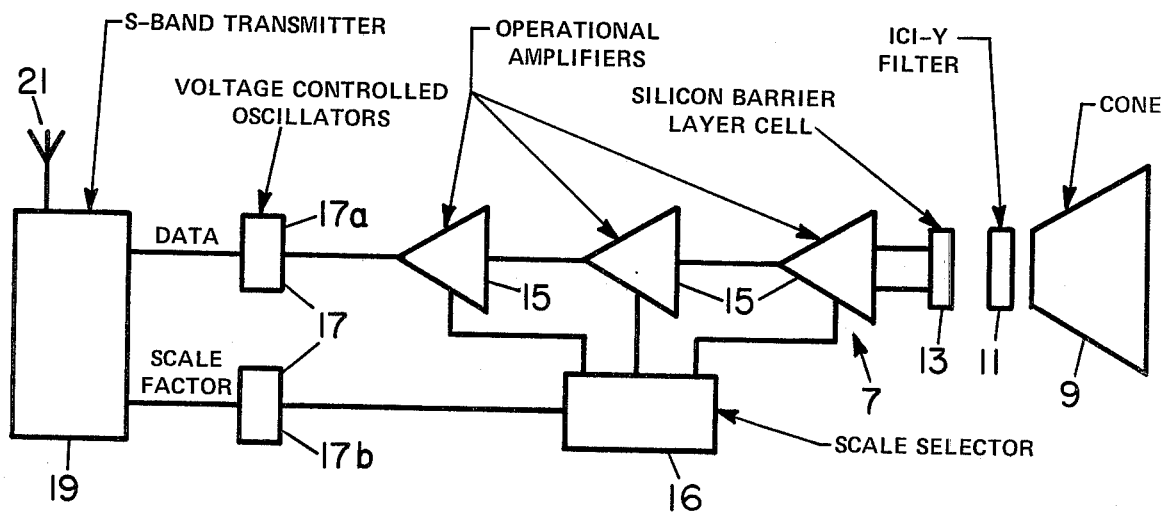
FIG. 2 is a schematic circuit of a field photometer that may be used for amplifying and transmitting each of the signals produced by three sensors in FIG. 1 to a remote base station.

FIG. 2 shows an example of a field photometer circuit 7 including one of the sensors $S_1$, $S_2$ and $S_3$ in FIG. 1, for measuring the illumination level E at that sensor and transmitting a corresponding electrical signal to a base station receiver. Each circuit 7 comprises a cone shield 9, an ICI-Y filter 11, a silicon barrier layer cell 13, three operational amplifiers 15, a scale selector 16, two voltage controlled oscillators 17, and an S-band transmitter 19 including an output antenna 21. Selector 16 is provided to select a suitable scale for the data signal on oscillator 17a and feed the scale signal to oscillator 17b. Each transmitter 19 produces a single carrier that is frequency modulated at two different frequencies by the two oscillators 17a and 17b.

Figure 3:
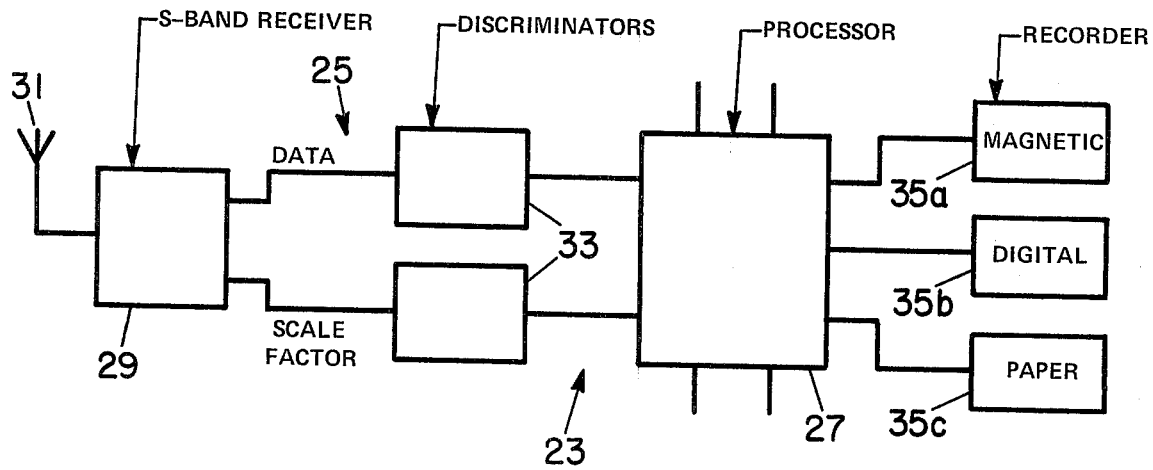
FIG. 3 is a schematic circuit of a base station apparatus for receiving the three signals and calculating and recording the transmissivity of the atmospheric medium.

FIG. 3 shows an example of a base station circuit 23 for receiving and processing the signals from the three photometer circuits 7. The circuit 23 comprises three identical receiver assemblies 25 (only one of which is shown) coupled to a processor 27. Each assembly 25 comprises an S band receiver 29, having an antenna 31, for receiving and de-modulating one of the three modulated carriers from the three transmitters 19, and two discriminators 33 for converting the data and scale signals to analog voltages, corresponding to the voltage inputs to the two oscillators 17a and 17b in FIG. 2. the processor 27 combines the three pairs of data and scale voltages to produce the original signals $E_1$, $E_2$ and $E_3$, and calculates the transmissivity of the optical medium, in accordance with equation (9), from the measured values of $E_1$, $E_2$ and $E_3$ and the known value of the spacing $d$ between the sensors 1, 2 and 3. The resulting transmissivity may be recorded or displayed by means of magnetic tape, digital and/or paper recorders 35A, 35B and 35C.

The apparatus shown in FIGS. 2 and 3 permits the substantially-instantaneous real-time display of the transmissivity while the light measurements are being made. However, it will be understood that the invention can be practiced by calculating the transmissivity in the field directly from the readings of the sensors 1, 2 and 3.

In the example considered above, the distances d and D are slightly less than one and two miles, respectively, and the apparatus is fixedly mounted on suitable supports. In another application of the invention, three small sensors could be mounted, with a spacing $d$ of 1 or 2 feet, on a suitable frame or bar hand-held by a soldier and aimed at a light source at an unknown distance D. This apparatus could include a micro processor connected to the three sensors for calculating and displaying the transmissivity of the atmosphere.

What is claimed is:

1. An apparatus for determining the transmissivity T of a gas medium on the basis of the following equation $$T = \left[ \sqrt{\frac{E_3}{E_2}} + \sqrt{\frac{E_3}{E_2} - \sqrt{\frac{E_3}{E_1}}} \right]^{2/d}$$

comprising the combination of a source of radiation in a gas medium, and three radiation sensors $S_1$, $S_2$ and $S_3$ for measuring the amounts of radiation $E_1$, $E_2$ and $E_3$ respectively received thereby from said radiation source in a gas medium, wherein (a) said sensors are aligned with each other and said radiation source will equal spacing $d$ between sensors $S_1$ and $S_2$ and sensors $S_2$ and $S_3$, the middle sensor $S_2$ being at an unknown distance D greater than d from said radiation source, and (b) said sensors are located at distances D−$d$ and D+$d$ respectively from said source, where d is smaller than D.

2. An apparatus according to claim 1, wherein the radiation source is an illuminating flare in the atmosphere and the radiation sensors are photometers.

* * * * *